US 9,554,713 B2

United States Patent
Frykman et al.

(10) Patent No.: US 9,554,713 B2
(45) Date of Patent: Jan. 31, 2017

(54) PROBE STIMULATOR

(71) Applicant: Global Pediatric Surgical Technology and Education Project, Inc., Irvine, CA (US)

(72) Inventors: Philip Kent Frykman, Malibu, CA (US); Keith J. Kimble, Los Angeles, CA (US)

(73) Assignee: Global Pediatric Surgical Technology and Education Project, Inc., Irvine, CA (US)

( * ) Notice: Subject to any disclaimer, the term of this patent is extended or adjusted under 35 U.S.C. 154(b) by 0 days.

(21) Appl. No.: 14/635,751

(22) Filed: Mar. 2, 2015

(65) Prior Publication Data

US 2016/0256061 A1  Sep. 8, 2016

(51) Int. Cl.
| | |
|---|---|
| *A61B 5/00* | (2006.01) |
| *A61B 5/04* | (2006.01) |
| *B23K 1/00* | (2006.01) |
| *B23K 1/19* | (2006.01) |

(52) U.S. Cl.
CPC ......... *A61B 5/04001* (2013.01); *A61B 5/4029* (2013.01); *A61B 5/4836* (2013.01); *B23K 1/00* (2013.01); *B23K 1/19* (2013.01); *A61B 2562/125* (2013.01); *B23K 2203/12* (2013.01)

(58) Field of Classification Search
None
See application file for complete search history.

(56) References Cited

U.S. PATENT DOCUMENTS

| | | | | | |
|---|---|---|---|---|---|
| 3,664,329 | A | * | 5/1972 | Naylor | A61B 5/05 600/554 |
| 4,033,356 | A | * | 7/1977 | Hara | A61N 1/0452 607/150 |
| 4,962,766 | A | * | 10/1990 | Herzon | A61N 1/36014 600/554 |
| 6,083,250 | A | * | 7/2000 | Lathrop | A61N 1/326 607/50 |
| 6,139,545 | A | * | 10/2000 | Utley | A61B 5/053 606/34 |
| 6,618,626 | B2 | * | 9/2003 | West, Jr. | A61B 18/148 606/34 |
| 6,801,808 | B2 | * | 10/2004 | Lee | A61N 1/32 607/115 |

(Continued)

OTHER PUBLICATIONS

Short, et al., "A Low-Cost Improvised Nerve Stimulator is Equivalent to High-Cost Muscle Stimulator for Anorectal Malformation Surgery," European Journal of Pediatric Surgery; Feb. 23, 2013; vol. 23 No. Jan. 2013; pp. 25-28.

*Primary Examiner* — Brian T Gedeon
(74) *Attorney, Agent, or Firm* — Erick J. Birkeneder; Nixon Peabody LLP

(57) ABSTRACT

A muscle stimulator that may be used during ARM surgeries is disclosed that may be constructed from (1) a widely available low cost (e.g., $200 per unit) peripheral nerve stimulators or similar stimulator and (2) a relatively simple, handheld surgical probe to provide a low cost muscle stimulator that is adequate for ARM surgeries. These two components could provide a low cost solution to allow doctors in developing countries feasibly perform ARM surgeries with relatively minimal manufacturing and inexpensive maintenance.

18 Claims, 3 Drawing Sheets

(56) References Cited

U.S. PATENT DOCUMENTS

| | | | | |
|---|---|---|---|---|
| 7,584,001 B2* | 9/2009 | Beck | ............... | A61N 1/32 |
| | | | | 607/145 |
| 8,083,685 B2* | 12/2011 | Fagin | ............... | A61B 5/04001 |
| | | | | 600/554 |
| 8,500,652 B2* | 8/2013 | Strother | ............... | A61B 17/1626 |
| | | | | 600/554 |
| 8,639,361 B2* | 1/2014 | Nathanson | ............... | A61N 1/328 |
| | | | | 607/145 |
| 9,044,232 B2* | 6/2015 | Cheng | ............... | A61B 18/082 |
| 9,241,753 B2* | 1/2016 | Fourkas | ............... | A61B 18/02 |
| 2004/0230359 A1* | 11/2004 | Sandstrom | ............... | F15B 19/002 |
| | | | | 701/51 |
| 2007/0073372 A1* | 3/2007 | Heath | ............... | A61N 1/20 |
| | | | | 607/145 |
| 2014/0371812 A1* | 12/2014 | Ackermann | ............... | A61N 1/36046 |
| | | | | 607/46 |

\* cited by examiner

PROBE STIMULATOR

FIELD OF THE INVENTION

The claimed invention relates to devices and methods for the stimulation of a patient's muscles using a probe.

BACKGROUND

Anorectal malformations are variety birth defects that may include (1) the absence of an anal opening, (2) the anal opening in the wrong place, (3), a connection, or fistula, joining the intestine and the urinary system, (4) a connection joining the intestine and vagina, or (5) the intestine can join with the urinary system and vagina in a single opening. During repair of the anorectal malformations, the colon is pulled down to a newly created anal opening, which must be properly situated between the anal sphincter muscles. Repair of anorectal malformations (ARM) using either posterior sagittal anorectoplasty (PSARP) or Georgeson's laparoscopic technique is optimally performed using a muscle stimulator to clearly delineate the anal and pelvic muscle complexes for precise anatomic placement of the rectal pull-through segment. Unfortunately, commercially available muscle stimulators for ARM surgery can be prohibitively expensive for many regions of the globe due as their cost may exceed 10,000 USD. Not surprisingly, this cost barrier limits the use of this critically important tool by surgeons in communities with limited resources to purchase this device.

BRIEF DESCRIPTION OF THE FIGURES

Exemplary embodiments are illustrated in referenced figures. It is intended that the embodiments and figures disclosed herein are to be considered illustrative rather than restrictive.

FIG. 2 depicts, in accordance with various embodiments of the present invention, a top view of a probe and stimulator; and.

SUMMARY OF THE INVENTION

Figure 1:
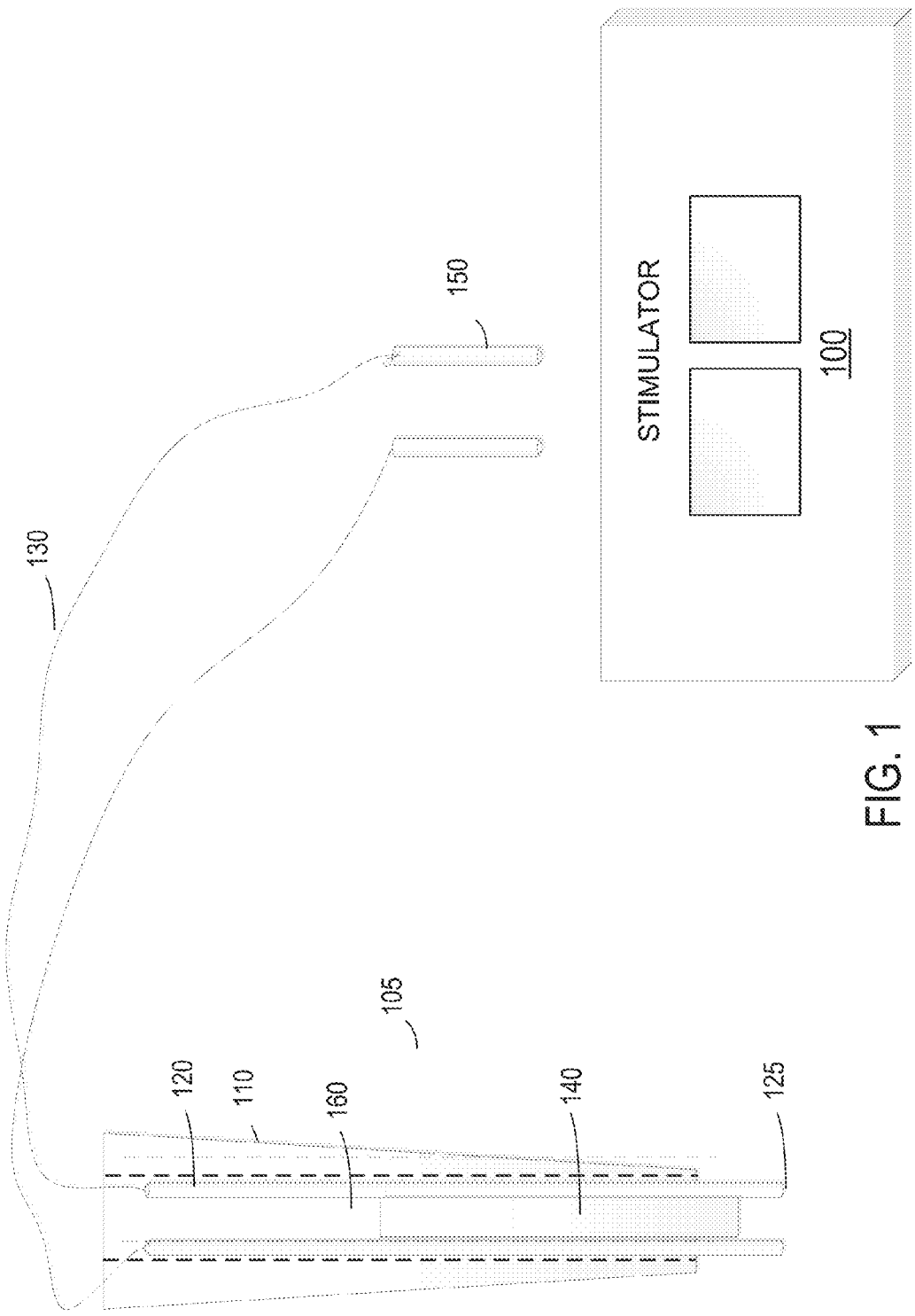
FIG. 1 depicts, in accordance with various embodiments of the present invention, a cross sectional view of a probe and stimulator.

Through various forms of experimentation, the inventors have determined that a suitable muscle stimulator may be constructed from (1) a widely available low cost (e.g., $200 per unit) peripheral nerve stimulators or similar stimulator and (2) a relatively simple, handheld surgical probe to provide a low cost muscle stimulator that is adequate for ARM surgeries. These two components could provide a low cost solution to allow doctors in developing countries feasibly perform ARM surgeries with minimal cost and manufacturing. Furthermore, a simple and durable probe stimulator may be easily detached from the device and sterilized using a steam (e.g. autoclave) sterilization procedure that is harsh but inexpensive. This is a drastic improvement over current muscle stimulators which have complex probes that cannot be steam sterilized and therefore require sterilization at a centralized hospital using potentially time intensive procedures.

Stimulator

In some embodiments, a commercially available "Peripheral Nerve Stimulator" commonly designed for use as a tool for anesthesiologists to determine the appropriate sedation levels for a given patient during surgery may be utilized to provide the appropriate electrical stimulation. There are various manufacturers of these devices, and they typically consist of an electronic device that is battery operated with some type of user interface controlling the amount of current that is delivered through various forms of metallic external connectors to the patient. The stimulator is activated through a button that delivers electrical current from the stimulator when depressed.

Probe

The second component of the presently disclosed device is the handheld surgery probe that may include a probe tool and an electrical connection to the stimulator that delivers the electrical current from the stimulator to the patient's skin. In some embodiments, such a handle held probe may include an electrically insulated handle with two metallic leads that protrude through the top of the device and deliver the electrical stimulation to a patient's skin. The probe may include a handle portion or casing that is made of an electrically insulating material to prevent the flow of current between the two metallic leads when not in contact with the patient's skin. The probe could be constructed from a material that can endure sterilization temperatures and is resistant to corrosion caused by the steam sterilization.

In some embodiments, the probe is connected to the stimulator through a pair of electrically insulated wires that connect from metallic leads on the pen probe to the two pins on the stimulator. The wires connecting the pen probe to the stimulation device may also be made of heat resistant and corrosion resistant materials so that the entire surgery probe unit can be separated from the stimulator device and sterilized and reused for multiple surgeries.

DETAILED DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. One skilled in the art will recognize many methods and materials similar or equivalent to those described herein, which could be used in the practice of the present invention. Indeed, the present invention is in no way limited to the methods described herein. For purposes of the present invention, the following terms are defined below.

Overview

FIG. 1 illustrates an embodiment of the present disclosure that includes a simulator 100 and a probe 105. The stimulator 100 may be connected to the probe 105 through a wire 130 and connector 150 or directly with just a wire 130. The probe 105 includes an electrically insulated casing 110 that house two leads 120 that conduct electricity to the patient's skin or soft tissue in order to stimulate muscles and/or nerves. In some embodiments, the leads 120 may contain a spacer 140 to ensure separation of the two leads 120 on the patient's skin.

During usage for example in an ARM surgery, a surgeon may place the probe leads 120 on a patient's skin and activate the simulator 100 to deliver a sufficient amount of electricity to a localized area in order to cause a contraction of muscle in the vicinity of the probe leads 120. If sufficiently electricity is delivered, the surgeon or a detector (for example with an EMG device) may record muscle contractions. Thus the surgeon will then be able to determine the location of certain muscles. For example, the device may be utilized to detect the location of the anal and pelvic muscles, so an appropriate placed incision can be made for the ARM surgery. If a contraction is detected, the intensity and direction of contraction will provide a surgeon or other caregiver with information regarding the location and orientation of muscles.

Stimulator

In some embodiments, stimulator 100 may be a conventional "Peripheral Nerve Stimulator" commonly designed for use as a tool for anesthesiologists to determine the appropriate sedation levels for a given patient during surgery. For example, the commercially available Micro Stim or SunStim peripheral nerve stimulators may be implemented. In other embodiments, any suitable stimulator 100 may be utilized that delivers an appropriate electrical pulse to two different leads as described herein.

The stimulator 100 may deliver a suitable pulse to cause contraction of muscles with a certain range of the leads 120 of the probe 105. For instance, the stimulator 100 may deliver a constant mode 100 Hz square wave that ranges between 0-70 milliamps. In other embodiments, other shapes of waves may be utilized that various in amplitude and frequency. In some embodiments, the amplitude may be varied to compensate for different ages of patients' that require a different threshold of stimulation to contract local muscles. The amplitude of current may also determine the maximum distance from the leads 120 that will precipitate muscular contraction. In some embodiments, the stimulator 100 may be able to vary the amplitude to allow a doctor to customize the pulse for a particular patient.

Figure 2:
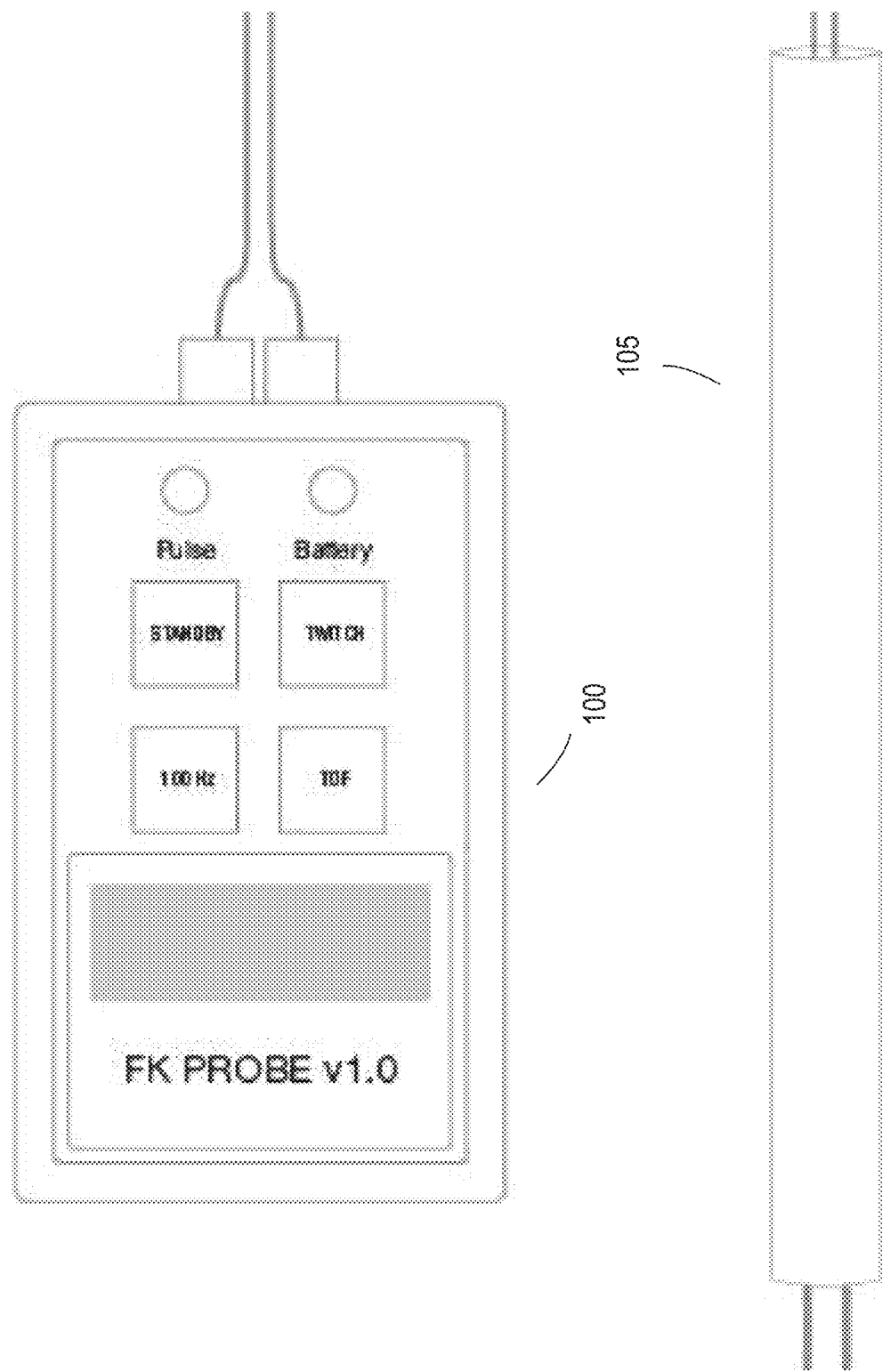

FIG. 2 illustrates an embodiment of the stimulator 100 including the available options for waveforms. As illustrated, the options available for stimulation are relatively basic and include a 100 Hz and TDF wave.

Probe

The probe 105 may be simply constructed from durable materials in order to allow for harsher sterilization methods that may be employed in developing countries. For instance, the probe 105 may include leads 120 for delivering the electrical current to a patient's skin from the wires 130. In some embodiments, the leads 120 may be elongated rods constructed of corrosion resistant metal or other conductors. In some embodiments, the leads 120 may be constructed from brass rods. In some embodiments, the ends of the leads 120 may be rounded at the tip 125 to avoid damaging a patient's skin. In some embodiments, the leads 120 may be 2-5 inches, 4 inches, 3 inches, 2 inches, or 1 inch, or other suitable lengths. FIG. 2 illustrates an embodiment of probe 105 that includes a relatively straight casing 110.

As illustrated in FIG. 1, casing 110 or other electrical insulating covering may enclose the leads 120 for handling by the physician and for preventing current from exiting the leads other than at the tip portion 125 of the leads. Various materials may be utilized for casing 110 that are preferably resistant to corrosive methods of sterilization, durable, and provide electrical insulation. For example, a polytretrafluoroethylene (PTFE) tube may be utilized, with holes or a channel for the leads 120 to be inserted through. In other embodiments, other materials may be utilized that are suitable.

In some embodiments, the casing 110 will have a channel 160 or hole that runs the longitudinal length of the tube. The leads 120 may be inserted through the hole and then a spacer 140 provided near the tip 125 to keep the leads 120 separated from each other. In some embodiments, spacer 140 may run the length of the casing 110, a third of the casing 110, or may be placed between the two leads 120. In other embodiments, the leads 120 may be glued to the side or spacer 140 with a cement or adhesive. In some embodiments, a filler may be packed into the hole 160 that could harden and keep leads 120 in place. In some embodiments, to lengthwise holes 160 may be drilled, machined, or otherwise made that are sized to fit leads 120. Casing may be rounded or sanded on the end nearest the tip 125 of the probes 120 to avoid a sharp protrusion.

The probes may be connected to connectors 150 or stimulator 100 through wires 130. Wires 130 may be any suitable wires that are resistant to certain types of corrosive and/or harsh sterilization techniques. For instance, 24 AWG, stranded wire may be utilizes that is rated for high heat, for example up to 150 C, 160 C, 170 c, or 200 C, and 600V with FEB insulation. The wire 130 may be connected to probe 120 and connector 150 by any suitable connection, including for example wrapping and soldering the wire to the leads 120 and the connector. In other embodiments, simple heat shrink tubing may additionally or alternatively be utilized that is rated for 140 C, 150 C, 160 C or other suitable temperatures.

Methods

The device as presently disclosed may be utilized for the stimulation of muscles during surgeries or in other appropriate contexts. For example, the stimulator 100 and probe 105 may be utilized to perform (1) repair of anorectal malformations (ARM) or (2) precise identification of facial nerve branches when performing head and neck surgery. Other examples and methods of utilizing a probe and stimulator as disclosed herein may be utilized for the stimulation of muscles of a patient.

Repair of anorectal malformations (ARM) using either posterior sagittal anorectoplasty (PSARP) or Georgeson's laparoscopic technique are optimally performed using a muscle stimulator to clearly delineate the anal and pelvic muscle complexes for precise anatomic placement of the rectal pull-through segment. Examples of these operations are described in detail in: Georgeson K E, Inge T H, Albanese Conn. (2000) Laparoscopically-assisted anorectal pull-through for high imperforate-anus—a new technique. J. Pediatr. Surg. 35:927-931.

Operations in which the identification of nerve branches is essential to safe operation include superficial parotidectomy and complete parotidectomy particularly in cases of parotid tumors. An example of this surgery is described in: Spiro R H., The parotid gland. In Baker R J, Fischer J E, eds. Mastery of Surgery. Vol. 14th ed. Philadelphia: Lippincott Williams & Wilkins; 2001: 320-327; and Pena A (1988) Posterior Sagittal anorectoplasty: results in the management of 332 cases of anorectal malformations. Pediatr. Surg. Int. 3:94-104.

Figure 3:
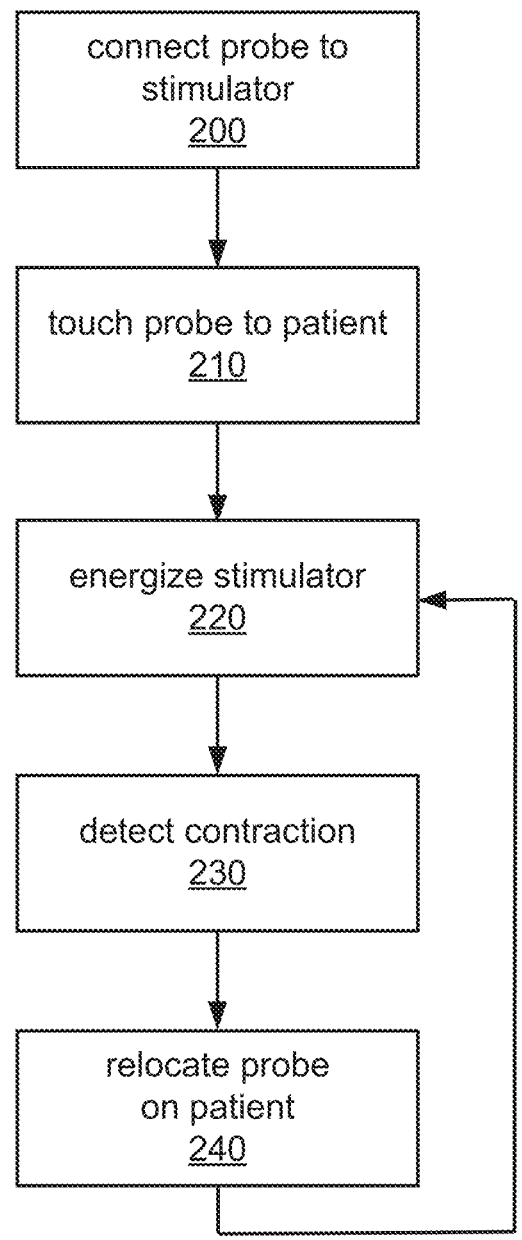
FIG. 3 depicts, in accordance with various embodiments of the prevent invention, a method for performing a surgery with the disclosed devices.

FIG. 3 illustrates an example of a method disclosed herein for utilizing the disclosed stimulating system. The methods disclosed may include providing a stimulator 100 that may be a conventional peripheral nerve stimulator, providing a probe as described herein. The stimulator 100 may be connected 200 to the probe 105 through a wire 130 and connector 150 or directly with just a wire 130.

The probe 105 and stimulator 100 may be utilized to map out the limits of the anal and pelvic muscle complexes for precise anatomic placement of the rectal pull-through segment. Accordingly, the probe 105 includes an electrically insulated casing 110 that house two leads 120 that conduct electricity to the patient's skin or soft tissue in order to stimulate muscles and/or nerves. In some embodiments, the leads 120 may contain a spacer 140 to ensure separation of the two leads 120 on the patient's skin.

During usage, for example in an ARM surgery, a surgeon may place the probe leads 120 on a patient's skin or soft tissue 210 and activate the simulator 220 to deliver a sufficient amount of electricity to a localized area in order to cause a contraction of muscle in the vicinity of the probe leads 120. If sufficiently electricity is delivered, the surgeon or a detector (for example with an EMG device), may record muscle contractions 230. Thus, the surgeon will then be able to determine the location of certain muscles. For example, the device may be utilized to detect the location of the anal and pelvic muscles, so an appropriate placed incision can be made for the ARM surgery. If a contraction is detected, the intensity and direction of contraction will provide a surgeon or other caregiver with information regarding the location and orientation of muscles. After a contraction is detected 230, the surgeon may relocate the probe on the patient 240 and repeat the process to map out the limits of the anal and pelvic muscles.

CONCLUSIONS

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventor for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A probe for electrical stimulation of a localized area of a patient's body, the device comprising:
   an insulating casing;
   a pair of electrically conductive leads wherein at least a portion of the leads are contained within a channel in the center of the casing; and
   a spacer at least partially contained within the channel and positioned between the pair of leads to prevent the pair of leads from contacting each other.

2. The probe of claim 1, wherein a pair of heat resistant wires are connected to the pair of leads.

3. The probe of claim 2, wherein a stimulator is connected to the pair of wires.

4. The probe of claim 3, wherein the stimulator is a peripheral nerve stimulator.

5. The probe of claim 1, where the spacer is comprised of PTFE.

6. The probe of claim 1, where the casing is comprised of PTFE.

7. The probe of claim 1, wherein the leads are brass rods.

8. A method of stimulating a patient's skin or soft tissue to identify muscular regions, the method comprising:
   providing a probe comprising a pair of leads at least partially enclosed by a casing and a spacer between the pair of leads;
   providing a peripheral nerve stimulator;
   electrically connecting the probe and stimulator;
   touching the stimulator to a patient's skin or soft tissue; and
   energizing the stimulator.

9. The method of claim 8, where the spacer is comprised of PTFE.

10. The method of claim 8, where the casing is comprised of PTFE.

11. The method of claim 8, wherein the leads are brass rods.

12. The method of claim 8, wherein the wires are soldered to the leads.

13. A method of manufacturing a probe for the electrical stimulation of a patient, the method comprising:
    connecting a pair of leads to a pair of wires;
    inserting the leads so that they are at least partially enclosed within a channel of a casing;
    inserting a spacer between the leads and at least partially enclosed within the casing; and
    connecting the pair of wires to a stimulator.

14. The method of claim 13, where the spacer is comprised of PTFE.

15. The method of claim 13, where the casing is comprised of PTFE.

16. The method of claim 13, wherein the leads are brass rods.

17. The method of claim 13, wherein the wires are soldered to the leads.

18. The method of claim 13, wherein the stimulator is a peripheral nerve stimulator.

* * * * *